(12) United States Patent
Lindquist et al.

(10) Patent No.: US 6,900,339 B2
(45) Date of Patent: May 31, 2005

(54) BRYOSTATIN COMPOSITION AND BRYOSTATIN ACQUISITION METHODOLOGIES

(75) Inventors: Niels Lindquist, Morehead City, NC (US); Nicole Lopanik, Lewes, DE (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 96 days.

(21) Appl. No.: 10/427,014

(22) Filed: Apr. 30, 2003

(65) Prior Publication Data

US 2003/0233000 A1 Dec. 18, 2003

Related U.S. Application Data

(60) Provisional application No. 60/376,398, filed on Apr. 30, 2002.

(51) Int. Cl.[7] .................. C07D 313/00; C07D 323/00
(52) U.S. Cl. ............................. 549/267; 549/268
(58) Field of Search ........................ 549/267, 268

(56) References Cited

U.S. PATENT DOCUMENTS

4,611,066 A    9/1986  Pettit et al. ............... 549/267

FOREIGN PATENT DOCUMENTS

EP          0 264 173         4/1988

OTHER PUBLICATIONS

*Chemical Abstracts* 129(21): abstract No. 272958k, p. 392 (1998).
*Chemical Abstracts* 132(2): abstract No. 10835j, p. 267 (1998).
*Chemical Abstracts* 132(26): abstract No. 345544v, p. 381 (1999).
Davidson, "Biology of the Bryostatins in the marine bryozoan *Bugula neritina*: Symbiosis, cryptic speciation and chemical defense," *Dissertation* University of California, San Diego, Margo G. Haywood, chair (1999).
Davidson et al., "Identification of Sibling Species of the Bryozoan *Bugula neritina* That Produce Different Anticancer Bryostatins and Harbor Distinct Strains of the Bacterial Symbiont '*Candidatus* Endobugula sertula,'" *Biol. Bull.* 196: 272–280 (Jun. 1999).
Haygood et al., "Bacterial Symbionts of the Bryostatin–Producing Bryozoan *Bugula Neritina*," *New Developments in Marine Biotechnology* Le Gal and Halvorson, eds. 281–284 (1998).
Haygood et al., "Small–Subunit rRNA Genes and In Situ Hybridization with Oligonucleotides Specific for the Bacterial Symbionts in the Larvae of the Bryozoan *Bugula neritina* and Proposal of *Candidatus* Endobugula sertuna," *Applied and Environmental Microbiology* 63(11):4612–4616 (Nov. 1997).

"Helping to Cure Cancer Through In–The–Sea Culture of Pharmaceuticals," *NCRI News* 9(3):3–5 (Jan. 1996).
Houwen et al., "Bryostatin 19: A New Antineoplastic Component from *Bugula neritina* in the South China Sea," English abstract (1998).
Houwen et al., "Studies on the Antineoplastic Constituents from Marine Bryozoan *Bugula neritina* in the South China Sea," English abstract (1998).
Houwen et al., "Studies on the Antineoplastic Constituents from Marine Bryozoan *Bugula neritina* Inhabiting South China Sea (III): Isolation and Structural Elucidation of bryostatin 10, 11, and 18," English abstract (2000).
*International Search Report* PCT/US03/13447, mailed Sep. 11, 2003.
Lindquist et al., "Palatability and Chemical Defense of Marine Invertebrate Larvae," *Ecological Monographs* 66(4):431–450 (1996).
Lindquist et al., "Timing of larval release by two Caribbean demosponges," *Marine Ecology Progress Series* 155: 309–313 (1997).
Lopanik et al., "Chemical and Molecular Characterization of Ontogenetic Shifts in the Chemical Defense in *Bugula neritina* (Bryozoa)," 2002 Ocean Sciences Meeting.
Lopanik et al., "Chemical and molecular characterization of ontogenetic shifts in the chemical defense in *Bugula neritina* (Bryozoa)," 31st *Marine Benthic Ecology Meeting* Florida State University (Mar. 21–24, 2002).
Lopanik et al., "Chemical defense of *Bugula neritina* (Bryozoa) larvae by bryostatins," 30th *Benthic Ecology Meeting* University of New Hampshire (Mar. 15–18, 2001).
Mendola, "Aquacultural Production of Bryostatin 1 and Ecteinascidin 743," *Drugs from the Sea* Fusetani N, ed.: 120–133 (2000).
Pettit et al, "Antineoplastic Agents. 340. Isolation and Structural Elucidation of Bryostatins 16–18," *J. Nat. Procl.* 59: 286–289 (1996).
Pettit et al., "Antineoplastic Agents. 224. Isolation and Structure of Neristatin 1," *Journal of the American Chemical Society* 6693–6695 (1991).
Pettit et al., "Isolation and Structure of Bryostatin," *J. Am. Chem. Soc.* 104: 6846–6848 (1982).
Pettit et al., "Isolation and Structure of Bryostatins 14 and 15," *Tetrahedron* 47(22): 3601–3610 (1991).

Primary Examiner—Ba K. Trinh
(74) Attorney, Agent, or Firm—Myers Bigel Sibley & Sajovec, P.A.

(57) ABSTRACT

Methods for obtaining bryostatins from the marine bryozoans of the *Bugula neritina* species complex are provided wherein the methods involve the extraction and purification of bryostatins from the larvae of *Bugula neritina* organisms. Further, the present invention relates to a novel bryostatin composition that can be extracted from *Bugula neritina*.

17 Claims, 9 Drawing Sheets

BRYOSTATIN COMPOSITION AND BRYOSTATIN ACQUISITION METHODOLOGIES

CROSS-REFERENCE TO RELATED APPLICATIONS

This application claims the benefit of, and incorporates herein by reference in its entirety, the following U.S. Provisional Application: U.S. Provisional Application No. 60/376,398, filed Apr. 30, 2002.

FIELD OF THE INVENTION

This invention generally relates to bryostatin compounds and the acquisition of bryostatins from *Bugula neritina*. More particularly, the present invention provides methods and processes for acquiring bryostatin compounds from *Bugula neritina* and a novel composition of matter, designated bryostatin 20.

BACKGROUND OF THE INVENTION

During the 1980's, compounds comprising a series of structurally related complex polyketides were investigated for there antineoplastic properties. The compounds, named bryostatins, were isolated from the marine bryozoan, *Bugula neritina*, a sessile marine invertebrate that filters plankton and other particles from the water column. One of these compounds, bryostatin 1, was shown to be particularly effective against leukemia. Since the time of the initial finding of bryostatin 1, numerous other bryostatins have been discovered, pharmacologically tested, and shown to also significantly inhibit the proliferation of cancer cells in vitro and in in vivo animal studies. For example, U.S. Pat. No. 4,560,774 discloses the compositions and structures of bryostatins 1 to 3; U.S. Pat. No. 4,611,066 discloses the compositions and structures of bryostatins 4 to 8; and U.S. Pat. No. 4,833,257 discloses the compositions and structures of bryostatins 9 to 13. In all, nineteen bryostatin compositions and structures are known and have been identified.

The most prominent source of bryostatins is the organism *Bugula neritina*, a marine bryozoan; some bryostatins have been isolated from other marine invertebrates but these samples were reported to be contaminated with colonies of *Bugula neritina*. *Bugula neritina* is a common fouling organism found in virtually all temperate regions of the world's oceans. It occurs as bushy colonies, branching biserial to about 10 cm high. Typically a brown-purplish color, the organisms may be found attached to many surfaces in coastal and estuarine environments, including rock jetties, floating docks, and on the bottoms of ships and boats. More recently, man-made aquacultural environments and man-made oceanic aquacultural environments have been studied for growing *Bugula neritina* under more controlled conditions. The focus of these studies has been to attempt to produce a sufficient, easily harvestable biomass of *Bugula neritina* from which commercially viable quantities of bryostatins could be isolated.

However, the reported yields of bryostatins from *Bugula neritina* are extremely low. For instance, bryostatins are typically reported to occur in concentrations on the order of $10^{-6}$ to $10^{-8}$ percent *Bugula neritina* wet mass. Existing methods for the recovery of bryostatins from *Bugula neritina* requires the destructive harvesting and processing of the organism. To obtain usable quantities of bryostatins, an enormous biomass of *Bugula neritina* must be harvested and processed. A couple of methods have been proposed and tested for the harvesting of the *Bugula neritina* for bryostatin acquisition. One proposed harvesting method involves the collection of wild *Bugula neritina* growing in natural coastal environments. For example, to acquire sufficient quantities of bryostatin 1 just to conduct Phase I clinical trials, the National Cancer Institute collected and processed 12,712 kilograms of *Bugula neritina* to obtained approximately 18 grams of bryostatin. However, concerns about environmental impacts resulting from over-collecting and the possible decimation of local populations of *Bugula neritina* have led to the desire to develop alternative methods for growing and harvesting the organism. In response to this need, man-made aquacultural environments have been developed to grow *Bugula neritina* for harvesting and processing for bryostatins. The man-made aquacultural environments appear to be promising and offer some hope that large amounts of *Bugula neritina* organisms may be grown to meet the eventual biomedical and other research and commercial demands for bryostatins.

For instance, CalBioMarine, Inc., a California corporation, has developed methods for initiating the growth of *Bugula neritina* organisms on plastic or polymer plates in a controlled, man-made aquatic environment. After establishing seed populations of *Bugula neritina* on artificial, plastic plates, these substrates with growing *Bugula neritina* are transferred to an ocean environment where *Bugula neritina* growth is vigorous. These plates with attached *Bugula neritina* may be removed from the ocean for the harvesting and subsequent chemical processing of the *Bugula neritina*. The plates may be cleaned and reused for the next growth cycle by repeating the process described above. In addition to being expensive, this form of growing and harvesting *Bugula neritina* is also susceptible to failure at several points in the process. For example, if the *Bugula neritina* used to seed the plates do not initially grow well, an entire season's crop may be lost. To minimize some of these potential problems, other growth and harvesting strategies have been proposed for the aquaculture-base growth of *Bugula neritina*. For example, "clip-harvesting" of *Bugula neritina* growing on plates suspended in ocean waters has been proposed as an alternative harvesting method. Using clip harvesting, the entire *Bugula neritina* organism is not destroyed. This allows the *Bugula neritina* to re-grow after a portion is clipped from each colony. It is hypothesized that the clip-harvesting method may eliminate the costly process of seeding the plates with new *Bugula neritina* each year, as well as the need to monitor and control the growth of the *Bugula neritina* on the plates in a man-made environment until such time that they may be transferred to the ocean for further growth. However, relative to a completely destructive harvest, larger standing stock of *Bugula neritina* must be maintained for clip harvesting to acquire the same biomass of *Bugula neritina* to attain a given amount of bryostatins. Further, the costs of clip harvesting, while possibly lower than the destructive harvesting, are still high.

One major problem associated with acquiring bryostatins from *Bugula neritina* is the exceedingly low levels of bryostatins in *Bugula neritina*—typically in the range of $10^{-6}$ to $10^{-8}$ percent wet mass of the animal. Using current processing techniques, large quantities of the *Bugula neritina* must be harvested and processed to extract very small concentrations of bryostatins from the organism, which substantially increases the costs of removing and purifying brysotatins from harvested *Bugula neritina*. During processing, the bryostatins are extracted from the *Bugula neritina* along with numerous other compounds produced by the animal. The bryostatins must then be purified from the complex mixture of chemicals in this extract. The purification of bryostatins from the *Bugula neritina* extract requires a great number of man-hours, the use of large amounts of chemicals, and expensive processing equipment, such as preparative-scale chromatography systems. Solvents typically used in the processing steps create health and safety hazards, pose environmental concerns, and increase the costs of processing. In addition, large amounts of solvent treated *Bugula neritina* organisms must be disposed of following processing. The overall costs of processing *Bugula neritina* to obtain bryostatins are very high, thereby making the acquisition of commercial quantities of bryostatins from *Bugula neritina* uneconomical while limiting the amount of bryostatin produced annually.

A cost-effective and commercially scalable synthesis of bryostatins has not yet been developed, which has further hindered the biomedical development and commercialization of the bryostatins. Although numerous research groups are currently working on developing methods for the efficient, large-scale and economical synthesis of bryostatins, the structural complexity of the bryostatins has prevented the development of an economically viable synthesis and thus the commercial development of the bryostatins.

Given the major impediments discussed above for producing commercially viable quantities of bryostatin-based cancer drugs and valuable molecular probes, there exists a tremendous need and desire to develop new methods for obtaining bryostatins that are economically feasible. Furthermore, the development of new bryostatin compounds and structures is also desirable.

SUMMARY OF THE INVENTION

The present invention relates to novel methods for obtaining bryostatins from the marine bryozoans of the *Bugula neritina* species complex. More particularly, the present invention relates to methods of collecting *Bugula neritina* larvae and obtaining bryostatins from the collected larvae. Further, the present invention relates to the novel composition of matter, designated bryostatin 20, which is referred to as such throughout.

In various embodiments of the present invention *Bugula neritina* larvae are collected and processed to extract the bryostatins they contain. The collection of *Bugula neritina* larvae may be performed using various methods and processes and the larvae may be collected from wild *Bugula neritina*, *Bugula neritina* grown in a completely man-made aquaculture environment, or from *Bugula neritina* grown in a man-made, in-the-sea aquaculture environment. Extraction of bryostatins from the collected larvae may be accomplished using extraction processes identical to or similar to extraction processes previously reported for obtaining bryostatins from adult *Bugula neritina*. Still other extraction processes and methods may be employed.

In other embodiments of the present invention, *Bugula neritina* larvae are collected and stressed. The stressing of the *Bugula neritina* larvae causes them to exude most of the bryostatins they possess. *Bugula neritina* larvae may be physically or chemically stressed to induce the exudation of bryostatins. The larval exudate, which is comprised almost entirely of bryostatins, is easily collected and processed to purify individual bryostatins. Optionally, the stressed larvae may also be processed to recover any residual bryostatins not exuded by the collected larvae. Alternatively, under some circumstances, the stressed larvae may be returned to an environment containing *Bugula neritina* where the stressed larvae may settle and reinforce the larval producing *Bugula neritina* colonies.

In still other embodiments of the present invention, *Bugula neritina* larvae are collected from reproducing populations of *Bugula neritina* and stressed to promote the exudation of bryostatin, and especially novel compositions of bryostatin, designated bryostatin 20, from *Bugula neritina* populations native to the North Carolina coastal ocean and estuarine environments. The bryostatin 20 compositions may be used as anticancer drugs, incorporated with anticancer drugs, or used as other medicaments.

BRIEF DESCRIPTION OF THE DRAWING FIGURES

The invention can be more readily ascertained from the following description of the invention when read in conjunction with the accompanying drawings in which.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention relates to methods for obtaining bryostatins from marine bryozoans of the *Bugula neritina* species complex. More particularly, the present invention relates to methods of collecting *Bugula neritina* larvae and obtaining bryostatins from the collected larvae. Embodiments of the present invention relate to methods for obtaining bryostatins from marine bryozoans of *Bugula neritina* species complex without necessitating the destruction or harvesting of adult *Bugula neritina*, which produce and release bryostatin containing larvae. Various methods encompassed by the embodiments of the present invention provide for greatly enhanced yields of bryostatins from a given biomass of *Bugula neritina* without damaging or harvesting the adult colonies, relative to the amount of bryostatin that could be acquired from a one-time destructive harvest of an equivalent amount of adult *Bugula neritina* colonies.

It has been discovered that the free-swimming larvae of *Bugula neritina* contain bryostatins, just as the adult colonies of *Bugula neritina*, but, unexpectedly, at concentrations substantially greater than reported for adult *Bugula neritina*. In fact, the amount of bryostatins in larval tissues is 100 to 10,000 times (2 to 4 orders of magnitude) greater than the amount of bryostatins reported in equivalent amounts of adult tissue. This finding indicates that collection of *Bugula neritina* larvae and extraction of the bryostatins they contain may be a significantly more efficient means of acquiring bryostatins than the extraction of bryostatins from adult *Bugula neritina* using the traditional harvesting and processing techniques. An additional advantage of collecting bryostatins from the larval stage of *Bugula neritina* is that this bryozoan produces multiple batches of larvae over a reproductive season typically lasting several months each year. In contrast, *Bugula neritina* often has only on growing season each year, and for much of the year is found simply as a mass of basal tissue attached to the substrate with no upright growth. It has been determined that the *Bugula neritina* larvae use bryostatins to defend against predation, including against predation by the abundant omnivorous pinfish, *Lagodon rhomboides*. Levels of bryostatins found in adult *Bugula neritina* colonies do not appear to have a similar defensive function. Further, *Bugula neritina* larvae are able to exude their bryostatins, which allows the bryostatins to optimally deter predators.

As an example of the bryostatin concentration difference between larval and adult stages of *Bugula neritina*, it has been determined that bryostatins in *Bugula neritina* larvae are readily detected in as little as 10 µl of larvae or larval tissue using High Pressure Liquid Chromatography (HPLC) methodologies employing Photo-Diode Array (PDA) detection methods. In comparison, bryostatins in similar amounts of adult *Bugula neritina* tissue cannot be detected using the same HPLC methodologies. Furthermore, it has been found that *Bugula neritina* larval dry mass is comprised of about 1 percent to about 2 percent bryostatins. This is about 100 to about 10,000 times (2 to 4 orders of magnitude) greater than the amount of bryostatins reported in comparable amounts of adult tissues.

Studies also demonstrate that the concentration of bryostatins in *Bugula neritina* larvae decreases dramatically as the larvae age. FIGS. 1A-1D illustrate HPLC chromatograms recorded at 230 nm of larval extract from 10 µl of larval tissue at different time periods after the larvae settle and metamorphose into the attached benthic juvenile stage. Peaks at retention times of 16.2, 16.5, 18.0, 18.9, 19.8, 22.3, 24.2, and 26.6 minutes in FIG. 1A correspond to bryostatins. Similar, peaks correspond to the same bryostatins in FIGS. 1B-1D. The chromatograms indicate that the concentration of bryostatins in the tissue of newly settled and metamorphosed juvenile *Bugula neritina* rapidly decreases with increasing age after larval settlement.

Studies focused on *Bugula neritina* larvae indicate that the collection of bryostatins from the larval stage rather than the adult stage may be more feasible, requiring less manpower and resources, and thereby being commercially viable and profitable. Accordingly, various embodiments of the present invention include the recovery of bryostatins from *Bugula neritina* larvae.

In various embodiments of the present invention, *Bugula neritina* larvae are collected from adult *Bugula neritina* and then processed to extract the bryostatins from the larvae. The *Bugula neritina* larvae may be collected from reproductive adult colonies of *Bugula neritina* collected from natural habitats, obtained from man-made aquaculture environments, or obtained from man-made, in-the-sea aquaculture environments. Collection of the *Bugula neritina* larvae may be accomplished using various methods or processes. Extraction of bryostatins from the collected larvae may be accomplished using techniques similar to those reported for extracting bryostatins from large bulk collections of *Bugula neritina*, or by other processes and methods described below.

The process of collecting large quantities of *Bugula neritina* larvae begins with the establishment of a source population of adult *Bugula neritina*. Although *Bugula neritina* populations growing in the wild may be used with embodiments of the invention, *Bugula neritina* populations grown in man-made environments or in man-made environments in combination with in-the-sea grow ups are preferred. For example, *Bugula neritina* populations may be grown on artificial substrates and placed in water bodies conducive to the growth and health of the *Bugula neritina* population. The substrates upon which *Bugula neritina* populations are grown are preferably made from, but not limited to, strips of polyvinyl chloride (PVC) sheet plastic, lengths of polypropylene cord, plastic plates, and the like. Although various substrate sizes may be used for growing cultured *Bugula neritina* colonies, substrates of about 0.5 meters to about 1.0 meter long and about 0.25 meters to about 0.5 meters wide are preferred. *Bugula neritina* colonization of these substrates may occur by the initial settling of *Bugula neritina* larvae onto the substrate or by attaching adult colonies collected from native populations to the substrate. Adult *Bugula neritina* colonies or populations that are tied or strapped to the plates will eventually self-attach through the outward growth of their basal rhizoids. Water bodies conducive to vigorous growth of the colonies may include natural bodies of seawater, such as, but not limited to, bays sounds, oceans, and the like. Likewise, non-natural water bodies may also be used, such as flow-through recirculating tanks, recirculating ponds, and the like.

Once populated by juvenile or adult colonies of *Bugula neritina*, the substrates may be suspended in an appropriate body of water to provide a favorable growth environment for the *Bugula neritina* populations. The substrates may be suspended in the water body using different techniques; for example, the substrates may be suspended from ropes or wires strung between structures, like finger piers of a floating dock complex, in or over a body of water such that the substrates dangle in the water body. Other methods and systems may be used to maintain the populated substrates in the desired water body. While suspended in the water body, the *Bugula neritina* populations growing on the substrates are exposed to an environment that may enhance larval production and thus the continued production of bryostatins.

Other mechanisms may also be used to promote the growth of *Bugula neritina* populations. For instance, shade cloths may be suspended over the substrates to minimize fouling by seaweeds.

During the reproductive season, the *Bugula neritina* populations may be removed from their water body emplacement for the purpose of collecting their larvae. Ideally, larvae may be harvested daily or as conditions permit or dictate. The larvae may be harvested by placing the substrates populated with reproductive colonies of *Bugula neritina* into collection vessels containing fresh seawater. A volumetric ratio of 1:3 (*Bugula neritina* to seawater in the vessel) is typical, although this ratio may vary substantially without compromising the larval collection process. Because *Bugula neritina* is reported to release larvae beginning 2 to 3 hours after sunrise, it is preferable, but not absolutely required, that, the substrates with reproductive adult colonies are moved from their aquatic environment to collection vessels during the pre-dawn hours to ensure that the daily spawning of the larvae does not commence before the substrates are positioned in the collection vessels. Opaque covers may be placed over the collection vessels to retard the spawning process until desired. The collection vessels may be designed to hold one or more substrates and are often designed to hold between about 10 to about 20 substrate units at a time.

Removal of the opaque covers and exposure of the collection vessels to a bright light, such as sunlight, initiates the spawning process. Artificial light sources may also be used to initiate the spawning process. The seawater in the collection vessels may be aerated, although aeration may be suspended during the time that the colonies are exposed to light and releasing larvae. Larvae of *Bugula neritina* exhibit a strong positive phototaxic response after being released from the adult colony. Thus, newly released larvae swim upward toward the light and toward the surface of the seawater in the collection vessel, thereby gathering at the surface of the vessel, where the concentrated larvae are easily collected.

In some embodiments of the present invention, an inverted funnel, shaped cone, or other structure may be submersed in the seawater in the collection vessel to direct the movement of the larvae to a specific position within the collection vessel, thereby concentrating the larvae and facilitating their collection. In various embodiment of the present invention, the larvae will aggregate at the surface of the seawater, where they may be collected for the bryostatin extraction process.

According to particular embodiments of the invention, bryostatins are obtained from the collected *Bugula neritina* larvae by known extraction methods. Other extraction methods may also be used. For example, the collected larvae may be pipetted, spooned, or otherwise removed from a collection vessel and placed into cooled seawater, for example seawater in a vessel immersed in ice. The cooled seawater immobilizes the larvae and causes them to sink to the bottom of the container holding the cooled seawater. Once the chilled larvae sink to the bottom of the container, the seawater may be removed from the *Bugula neritina* larvae and an extraction solvent is added to the larvae to begin the extraction of bryostatins from the larvae. The larvae may be subject to numerous solvent washings or exposures to promote further extraction of the desired bryostatins. Various solvents may be used during the extraction process. For example, solvents such as methanol, dichloromethane, and mixtures of solvents may be used with various embodiments of the invention. The solvent rinses are then combined and evaporated, for instance by rotary evaporation, to dryness. Bryostains are then purified from the dried organic residue using processes such as vacuum flash C-18 chromatography and HPLC. Alternatively, the collected *Bugula neritina* larvae may be deposited directly into a solvent from a collection vessel for bryostatin extraction.

Some notable aspects of the present invention include the fact that *Bugula neritina* has a reproductive season lasting typically 1 to 2 months (sometimes twice a year, such as in North Carolina) and that this bryozoan produces multiple batches of larvae over its reproductive season. Therefore it maintains a relatively low standing stock of developing larvae at any one point during its reproductive period and daily releases a proportion of its developing larvae. New larvae begin to develop as older more competent larvae are released. Because the majority of the bryostatins in *Bugula neritina* are associated with their larvae, the one-time harvest of a reproductive adult yields relatively little bryostatin; in contrast, embodiments of the present invention harvest the daily production of bryostatin-rich larvae from reproductive *Bugula neritina* colonies, which if not captured results in the loss of the majority of the bryostatins produced over the lifetime of the colony.

The harvesting of *Bugula neritina* larvae from the *Bugula neritina* populated substrates may proceed throughout the entire reproductive season of a *Bugula neritina* population. The collection and processing of the *Bugula neritina* larvae spares the adult *Bugula neritina* organism populations. This process will also increase the annual yield of bryostatins per unit mass of *Bugula neritina* because the bryozoan *Bugula neritina* sequentially produces and releases larvae over a long reproductive season, allowing multiple collections of larvae from a single population of *Bugula neritina*. In addition, at least some bryozoan experience multiple reproductive seasons each year, which increases the amount of larvae produced each year by *Bugula neritina*. Using embodiments of the present invention, the annual bryostatin yield from a unit mass of adult *Bugula neritina* organism may be increased over destructive harvesting techniques presently used.

In various other embodiments of the present invention the *Bugula neritina* larvae need not be sacrificed in order to collect their bryostatins. The inventors have also discovered that the bryostatins are concentrated on the surface of the *Bugula neritina* larvae and that the larvae exude the majority of their bryostatins when stressed either physically or chemically. For example, the vigorous shaking of a solution containing *Bugula neritina* larvae stresses the larvae to a point where they exude 90 percent or more of their bryostatins. Similarly, the emersion of the *Bugula neritina* larvae in various chemical solutions triggers the exudation of bryostatins from the *Bugula neritina* larvae. The larval exudate may be collected following completion of the stressing and purified to recover the bryostatins exuded by the stressed *Bugula neritina* larvae.

Various embodiments of the present invention capitalize on the findings that the *Bugula neritina* larvae contain larger amounts of bryostatins than do the adult colonies of *Bugula neritina*. In addition, various embodiments of the present invention capitalize on the findings that *Bugula neritina* larvae exude bryostatins when stressed. According to embodiments of the present invention, bryostatins may be obtained in high yields from *Bugula neritina* larvae through the collection and purification of stressed larval exudate. For example, adult *Bugula neritina* populations may be raised or otherwise obtained during their reproductive season and their larvae collected. The collected larvae may be stressed, either physically or chemically, to promote the exudation or excretion of at least a portion of their bryostatins. The larval exudate may be separated from the larvae and purified to obtain the desired bryostatins. The larvae may be further processed to extract any remaining bryostatins from the larvae or the larvae may be returned to the adult *Bugula neritina* populations and allowed to settle among the populations to continue the growth cycle.

*Bugula neritina* larvae exude bryostatins when physically stressed. Physical stressing of the *Bugula neritina* larvae may be accomplished using different methods or processes. In some embodiments of the present invention, collected *Bugula neritina* larvae are transferred to a closed container of seawater and are shaken to induce a physical stress on the larvae. Stressed larvae are separated from the seawater containing the larval exudate, for example but not limited to, straining through a sieve. Bryostatins in the seawater containing the larval exudate are then removed from the seawater by solvent extraction. The seawater used with embodiments of the present invention may be filtered or unfiltered seawater, but in certain embodiments it is preferably filtered seawater. Other fluids that are not harmful to the larvae may also be used during the physically stressing process and separated from the larvae with the larval exudate. The shaking of the larvae in the closed container may last anywhere from a few moments to 10 or more minutes, with periods of shaking lasting between about 1 minute and about 5 minutes usually sufficient to stress the larvae into exuding a portion of their bryostatins. Vigorously stirring or otherwise disturbing solutions containing larvae may also induce physical stresses.

Seawater or other solutions used to stress and collect the larval exudate are separated from the larvae and saved for extraction. The physically stressed larvae may be transferred back to *Bugula neritina* populations to help further propagate and expand the *Bugula neritina* population. For example, larvae collected from *Bugula neritina* populations in collection vessels may be returned to the collection vessels and allowed to settle on the substrates among the *Bugula neritina* population. The collection vessels may be covered to exclude light and thus promote the dispersal of the larvae back onto the substrates and away from the surface of the seawater in the collection vessel. A significant number of the stressed larvae will settle on the substrates to grow and help maintain a dense population of *Bugula neritina* on the substrates. Following the settelement of the stressed larvae onto the substrates, the substrates may be removed from the collection vessels and returned to their aquatic environment. The collection procedure may then be repeated every day or every-other day throughout the reproductive season of the *Bugula neritina* populations.

*Bugula neritina* larvae may also be chemically stressed to induce release or exudation of bryostatin. In various embodiments of the present invention, collected *Bugula neritina* larvae are transferred to a stressful chemical environment. The chemical environment induces stresses upon the larvae, causing the larvae to release or exude bryostatin. The larval exudate may be collected and purified to obtain the exuded bryostatin.

For example, *Bugula neritina* larvae were collected from *Bugula neritina* populations and placed in a solution of magnesium chloride that was isotonic with seawater. The larvae quickly faded from dark brown to a creamy-white color in less than a minute, indicating that the larvae had exuded bryostatin. Analysis of the stressed larvae showed an absence of bryostatins, also indicating that the bryostatins were exuded in the solution of magnesium chloride.

The *Bugula neritina* larvae may be chemically stressed using various salt solutions. Examples of some salt solutions that may be used include magnesium chloride solutions, potassium chloride solutions, and other aqueous salt solutions. The salt solution may include, but is not strictly limited to, between about 0.10 molar salt solution to about 2.0 molar salt solution. For example, 0.56 molar potassium chloride salt solutions have been found sufficient to chemically stress or shock *Bugula neritina* larvae and to cause the exudation of bryostatins. One indicator of the extraction of bryostatins from the *Bugula neritina* larvae is the apparent bleaching of the larvae under stress. When stressed, the dark brown color of the larvae fades to a creamy white color, apparently corresponding to the exudation of bryostatins from the larvae. Once stressed, the salt solution and larval exudate may be removed from the larvae and transferred to bryostatin extraction and purification processes.

According to embodiments of the present invention, salt solutions used to stress the *Bugula neritina* larvae and solutions used to physically stress the *Bugula neritina* larvae may be processed to collect the bryostatins exuded by the larvae. In some embodiments, organic solvents that are immiscible with the "stress solutions" may be added to the stress solutions to extract the bryostatins from the stress solutions. Examples of organic solvents that may be used with the embodiments of the invention include dichloromethane, ethyl acetate, butanol, and/or mixtures thereof. Other organic solvents suitable for extracting bryostatins from an aqueous solution may also be used. The collected and combined organic solvents used to strip the bryostatins from the stress solution may be evaporated to form a residue. This may include organic solvents from a single extraction of the stress solution or a combination of organic solvent extractions of the same stress solution. For example, the stress solution may be washed or extracted with organic solvent three times and the organic extraction solvents from each wash combined and evaporated to form a residue. Individual bryostatins in the residue may be purified using analytical, semi-preparative, or preparative HPLC, for example using reverse-phase systems such as C18 ODS columns, using either a gradient elution with a methanol/water mixture or an isocratic elution with various methanol/water mixtures. The selection of the elution to use may depend upon the elution time of the target bryostatin being collected.

The elution of individual bryostatins according to embodiments of the invention may be monitored using ultra-violet or photo-diode array detection methods. Further, the identification of individual bryostatins may be confirmed by the co-injection of known standards and by proton NMR and high-resolution mass spectrometry.

Figure 1A:
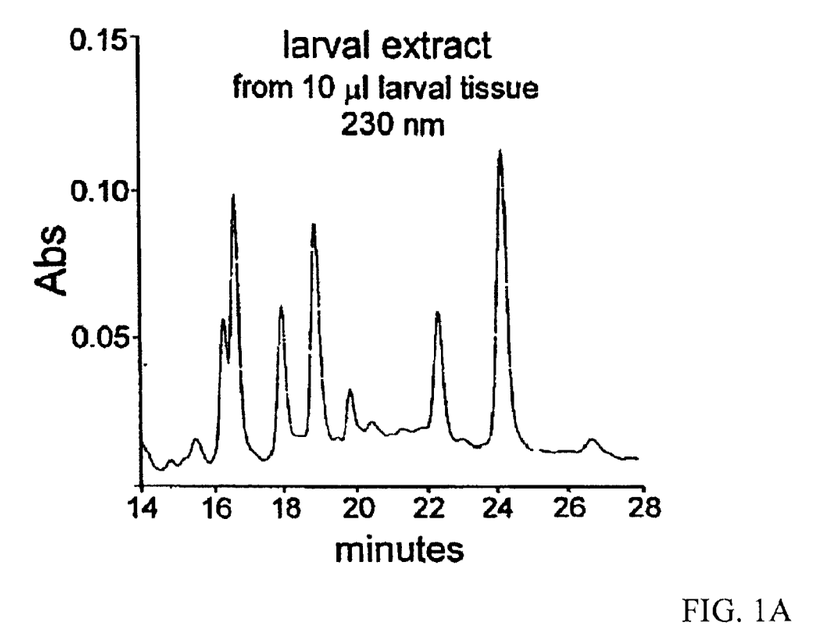
FIGS. 1A–1D illustrate chromatographs of larval tissue over time, wherein the chromatographs illustrate the amount of bryostatins present in the larval tissue.
Figure 1B:
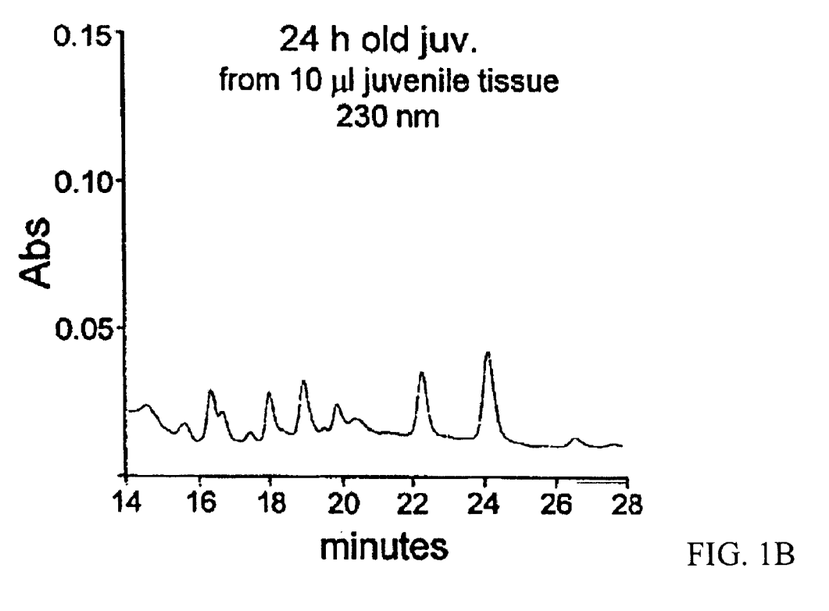
Figure 1C:
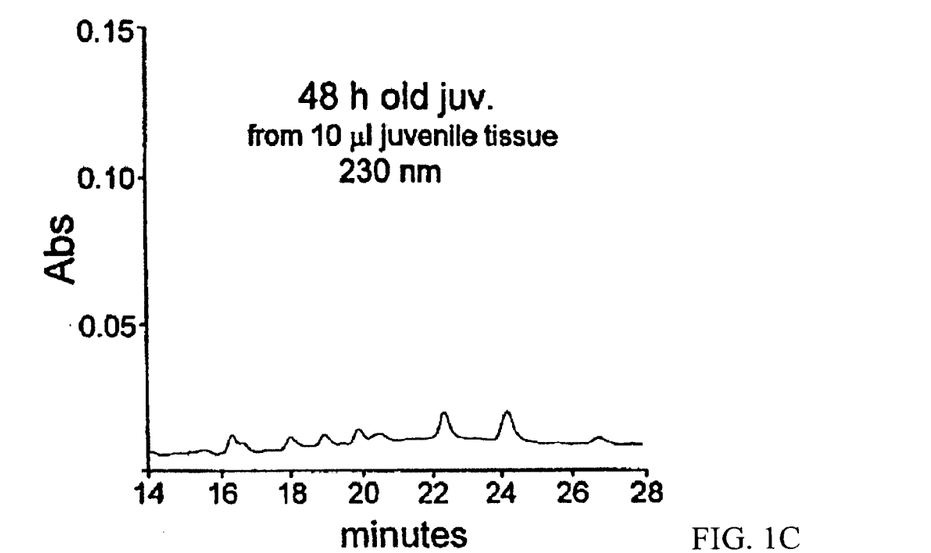
Figure 1D:
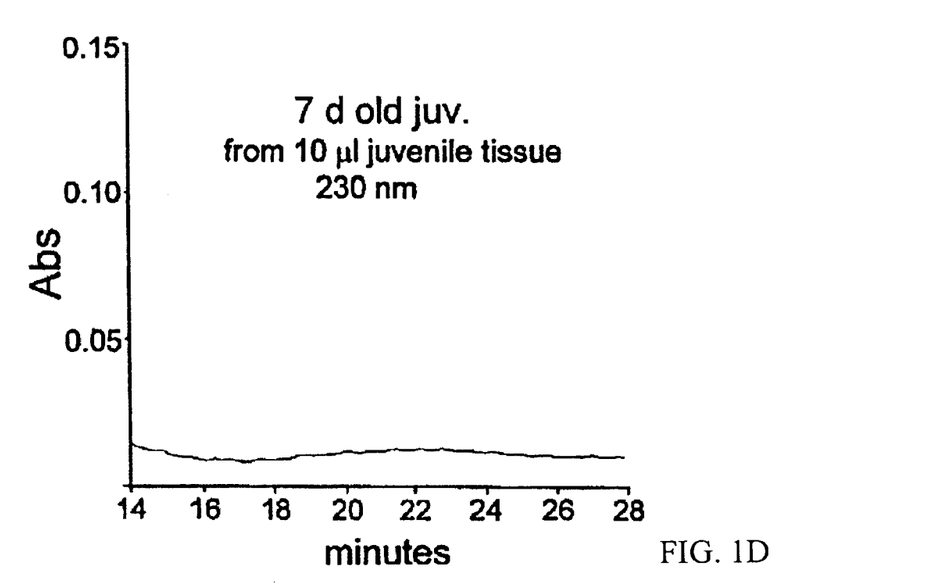
Figure 2:
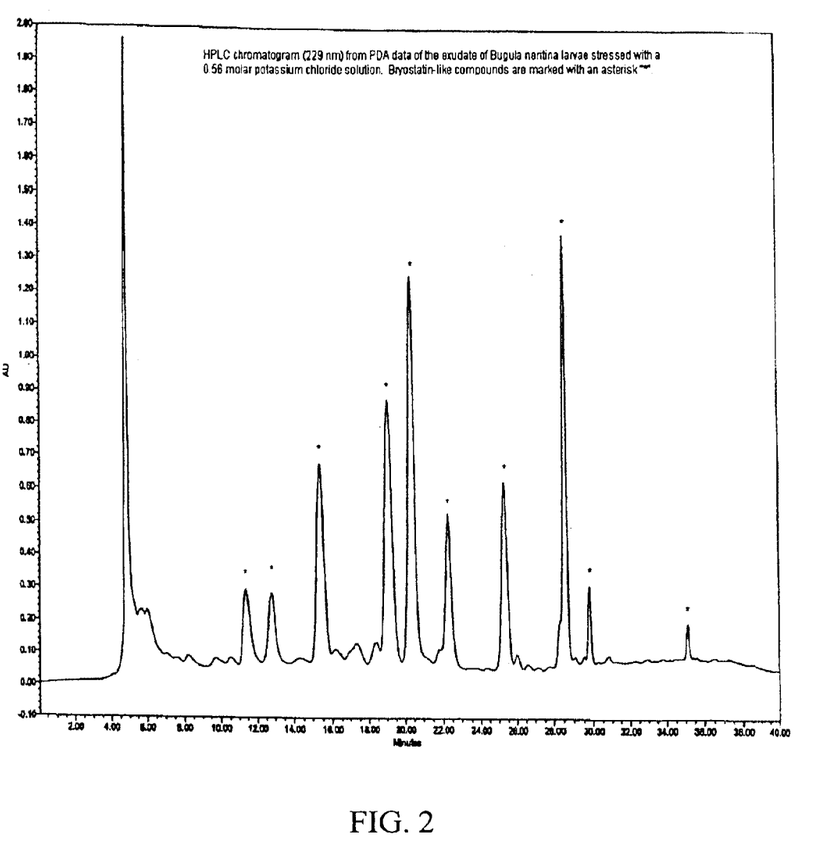
FIG. 2 illustrates an HPLC chromatogram at 229 nm from PDA data of the exudate of *Bugula neritina* larvae stressed with potassium chloride solution.
Figure 3:
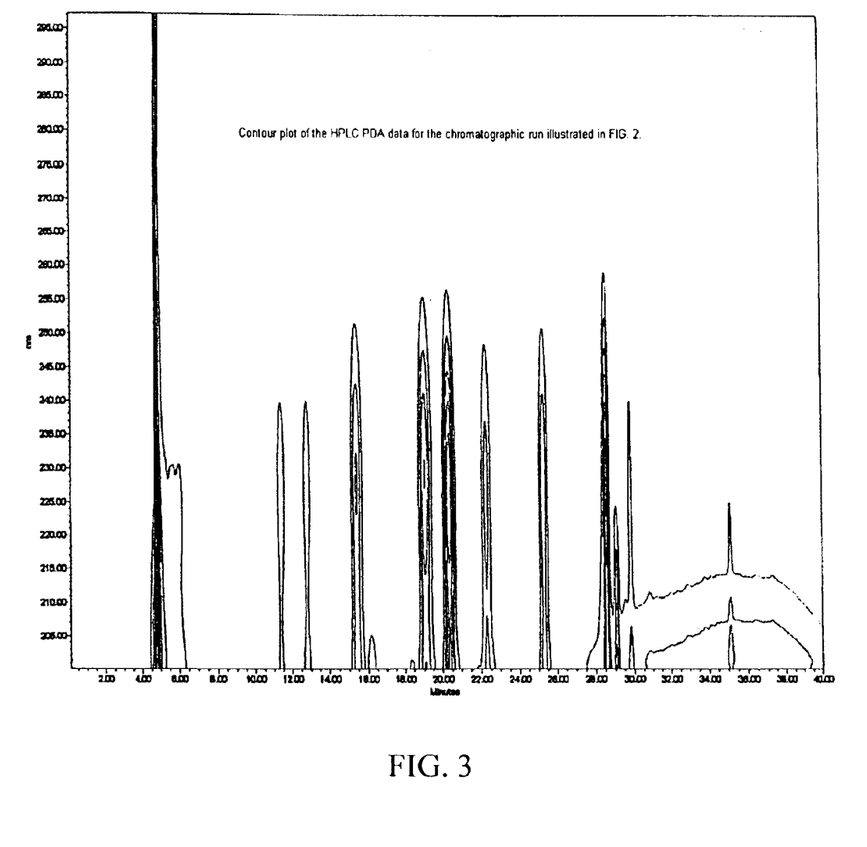
FIG. 3 illustrates a contour plot of the HPLC PDA data for the chromatograph of FIG. 2.
Figure 4:
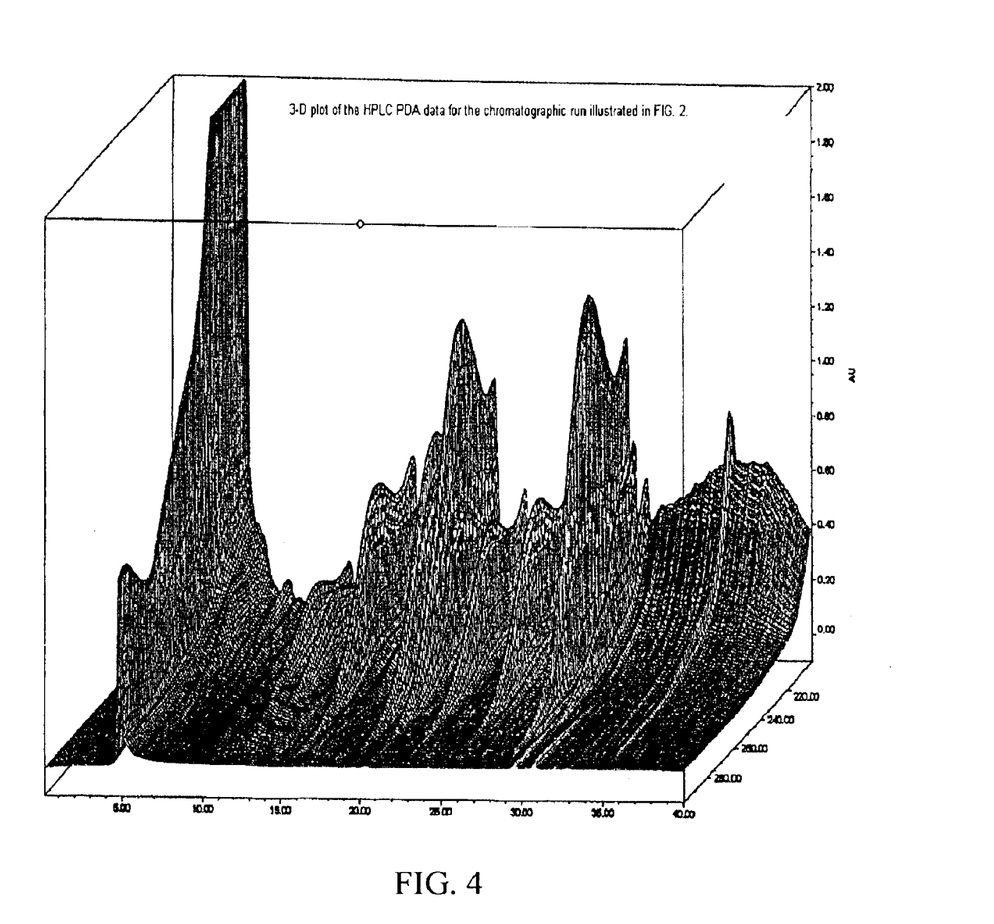
FIG. 4 illustrates a three-dimensional plot of the HPLC PDA data for the chromatograph of FIG. 2.
Figure 5:
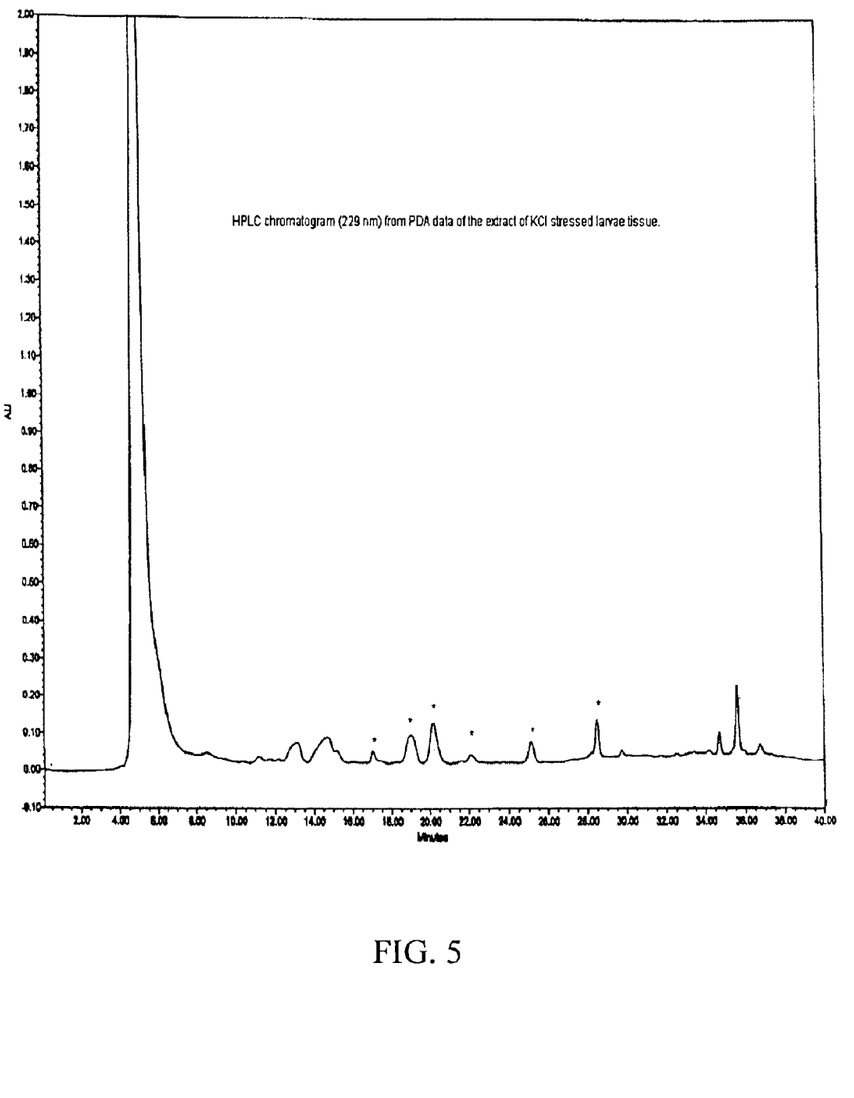
FIG. 5 illustrates an HPLC chromatogram at 229 nm from PDA data of *Bugula neritina* larva after the exudation of the exudate illustrated in FIG. 2.

In an example of an embodiment according to the present invention, approximately 1 liter of reproductive colonies of *Bugula neritina* were placed in 4-liter glass jars filled to within 1 cm of the top with seawater. The jars were exposed to a bright light to stimulate *Bugula neritina* to release its larvae. The bright light sources included natural sources, such as sunlight, and/or artificial sources, such as lamplight. Because the *Bugula neritina* larvae are positively phototatic, they swim to the surface of the seawater and aggregate along the rim of the jars upon exposure to the light. The larvae were collected by gently using a pipette. The collected larvae were transferred to a container outfitted with a bottom made of plastic NITEX mesh (100 $\mu$m) (container volume approximately 50 ml), which sat in a slightly larger container of seawater. After collecting larvae for 30 minutes, the mesh-bottomed container was gently removed from the seawater container. Immediately after the seawater drained out, the mesh-bottom container with the larvae was placed into a container holding a volume of a 0.56 molar potassium chloride (KCl) solution isotonic with seawater that filled the container approximately 1 cm deep. After soaking in the potassium chloride solution for about one minute, the mesh-bottom container and the larvae it contained were removed from the potassium chloride solution. The bryostatins and any other liphophilic compounds exuded by the larvae were removed from the aqueous "shock" solution by extraction with dichloromethane (DCM), and then butanol, both of which are immiscible with aqueous solutions. The combined DCM and butanol extractions were dried by rotary evaporation. The residue was analyzed by C18 reverse-phase HPLC. The HPLC analysis of the residue is illustrated in FIGS. 2–4. The HPLC analysis of the residue sample shows at least 10 peaks, 8 of which are major metabolites, in the chromatogram having a UV-absorption typical of most bryostatins. This HPLC analysis also shows that the larval exudate obtained by this method contains almost exclusively bryostatins. Furthermore, HPLC analysis of the extract of potassium chloride stressed larvae shows that they contained less than 10 percent of their original undisturbed bryostatin load. This is illustrated in FIG. 5. Proton NMR and mass spectral analysis of several of the major peaks in the exuded chemistry, two of which were found to be unpalatable to the fish *Lagodon rhomboides*, confirmed that the extracted compounds were indeed bryostatins.

In other embodiments of the present invention, *Bugula neritina* larvae may be subjected to any condition that causes them to extrude bryostatins. The extrudate may be collected from the larvae. The extrudate may also be purified to isolate specific bryostatins.

In other embodiments of the present invention, a combination of *Bugula neritina* larvae collection and adult *Bugula neritina* harvesting and processing may be used to obtain bryostatins. For instance, larvae may be collected during the useful reproductive season of a *Bugula neritina* organism population. Bryostatins may be extracted form the larvae according to various embodiments of the present invention. Following the useful reproductive season of adult *Bugula neritina*, the adult *Bugula neritina* may be harvested, or clip harvested, and processed to extract additional bryostatins during the non-reproductive times of the year. New *Bugula neritina* organisms may be grown to replace the old organisms destroyed by the harvesting.

In essence, *Bugula neritina* larvae function as a bryostatin concentrator. The collection and processing of *Bugula neritina* larvae to obtain bryostatins according to embodiments of the present invention increases the amount of bryostatins that may be collected per unit mass of adult *Bugula neritina*. Furthermore, the purification of bryostatins from *Bugula neritina* larvae and larval extracts according to various embodiments of the present invention is more efficient than the harvest of adult *Bugula neritina* and purification of the bryostatins from the extract as is currently employed. The aquaculture methods used by embodiments of the present invention recycle adult *Bugula neritina* populations to produce bryostatin-concentrated larvae instead of destructively harvesting the adults during the first growth cycle. Fewer solvents and chemicals are required by the processes and methods of the present invention, providing environmental benefits over the current bryostatin extraction processes. In addition, the processes and methods of various embodiments of the present invention are more cost-effective than existing processes and thereby providing for increased bryostatin production without huge capital expenditures.

In other embodiments of the present invention, a novel composition of matter, designated bryostatin 20, is provided. Bryostatin 20 may be extracted from *Bugula neritina* larvae according to embodiments of the present invention. Bryostatin 20 may also be extracted from *Bugula neritina* using traditional extraction techniques. The structure of Bryostatin 20 is identified by the formula illustrated in FIG. 6.

Collection of *Bugula neritina* from coastal waters in and around North Carolina produced *Bugula neritina* larvae that were collected according to embodiments of the present invention. Bryostatins from the collected larvae were extracted using the methods and processes of the various embodiments of the present invention. The purification of the extracted bryostatins according to the processes and methods of the present invention produced a composition having the structure illustrated in FIG. 6, which has not been previously identified. It is believed that bryostatin 20 is a new bryostatin composition unique to the *Bugula neritina* species living in the coastal waters of the Eastern United States, but it may also be found in *Bugula neritina* species living elsewhere.

Figure 6:
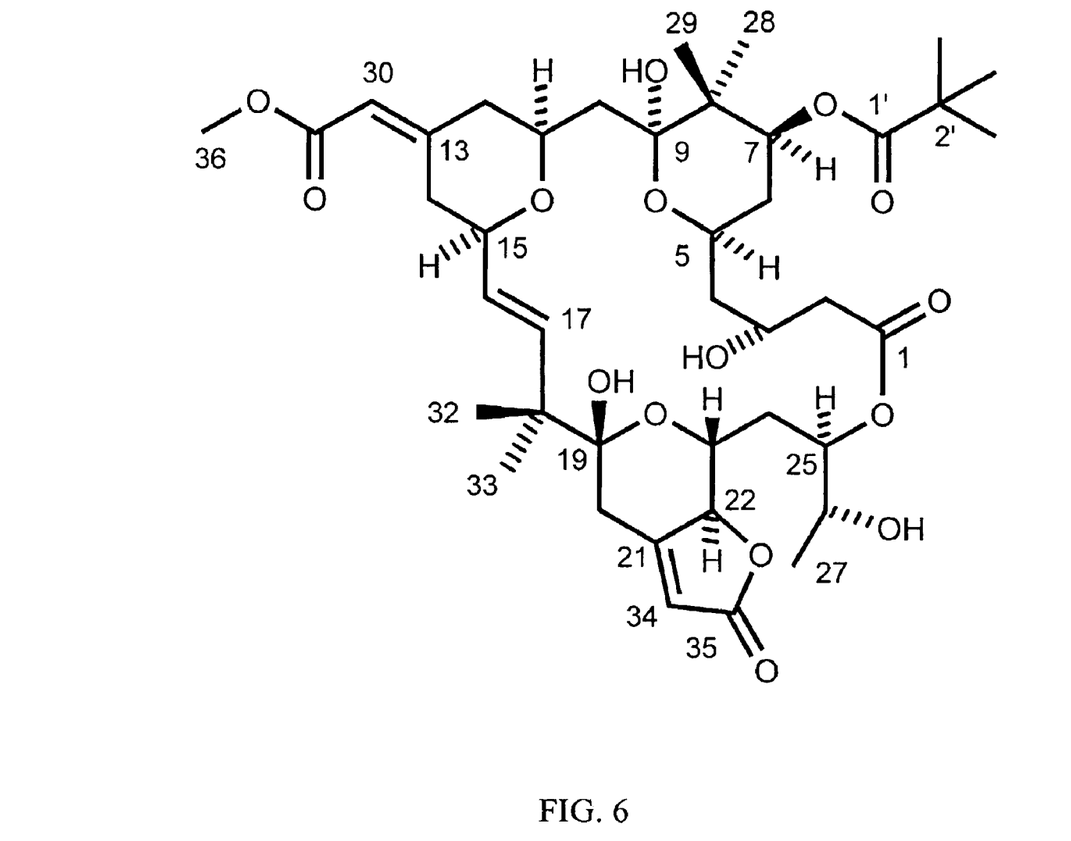
FIG. 6 illustrates the novel composition of the invention, designated bryostatin 20.

Mass spectral data and $^1$H and $^{13}$C-NMR data from tests performed on the composition, designated bryostatin 20, confirm the structure illustrated in FIG. 6. Mass spectrometry testing performed on the composition yielded results consistent with the proposed structure. In particular, Fast Atom Bombardment (FAB) using thioglycerol and a eutectic mixture of dithiothreitol and dithioerythritol ("Magic Bullet") as the matrix produced [M+Na]+ at 815.4, yielding a molecular ion of 792, which is consistent with the proposed structure. Fast Atom Bombardment using Magic Bullet doped with CsI produced [M+Cs]+ at 925.4, yielding a molecular ion of 792 and is consistent with the proposed structure.

Figure 7:
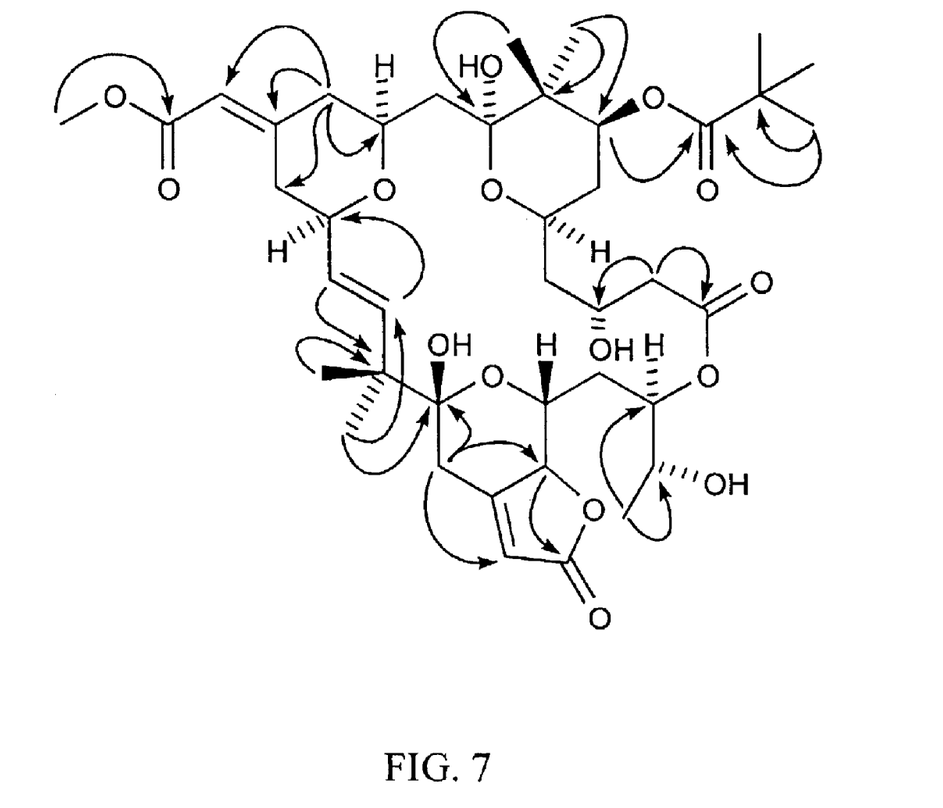
FIG. 7 illustrates selected HMBC correlations observed in the composition of the present invention, designated bryostatin 20.
Figure 8:
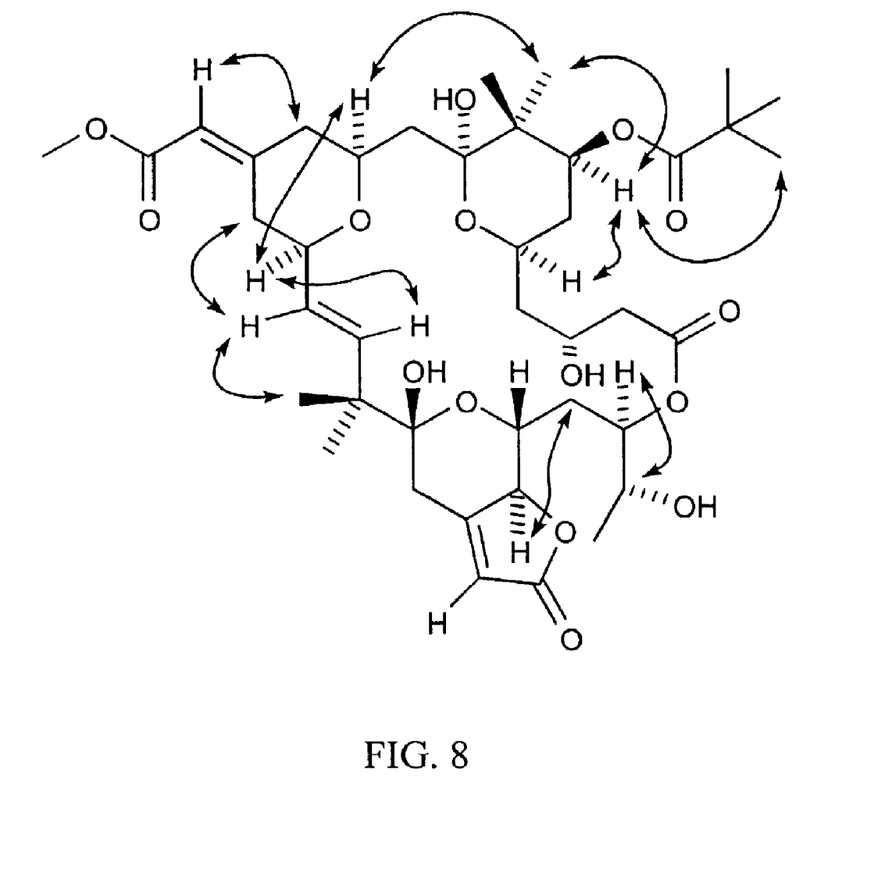
FIG. 8 illustrates selected NOE interaction observed in the composition of the present invention, designated bryostatin 20.

Data from the $^1$H and $^{13}$C-NMR testing of the composition designated bryostatin 20 is shown in Table I. Selected Heteronuclear Multiple Bond Connectivity (HMBC) correlations observed in the composition are illustrated in FIG. 7. Similarly, selected Nuclear Overhauser Effect (NOE) interactions observed in the composition are illustrated in FIG. 8.

TABLE I $^1$H and $^{13}$C NMR Data Obtained in CD$_3$CN for Bryostatin 20[a]

| pos. | $^1$H δ (J in Hz) | $^{13}$C δ |
|---|---|---|
| 1 |  | 172.01 |
| 2 | 2.50 br s, 2H | 41.62 |
| 3 | 4.00 m | 68.85 |
| 4 | 1.67 dt (3.5, 14.7) | 39.85 |
|   | 1.72 bd (14.7) |  |
| 5 | 4.18 tt (3.0, 11.8) | 65.83 |
| 6 | 1.43 q (12.0) | 33.00 |
|   | 1.62 ddd (3.0, 4.9, 12.6) |  |
| 7 | 5.08 dd (5.3, 12.1) | 72.28 |
| 8 |  | 41.54 |
| 9 |  | 101.31 |
| 10 | 1.72 bd (15.5) | 41.67 |
|    | 1.98 dd (7.1, 15.5) |  |
| 11 | 3.91 m | 72.55 |
| 12 | 2.17[b] 2H | 43.72 |
| 13 |  | 157.76 |
| 14 | 1.93[b] | 36.30 |
|    | 3.58 bd (13.8) |  |
| 15 | 4.10 m | 79.37 |
| 16 | 5.36 dd (8.4, 16.1) | 131.10 |
| 17 | 5.80 d (16.1) | 138.01 |
| 18 |  | 44.85 |
| 19 |  | 101.56 |
| 20 | 2.48 d (12.4) | 41.51 |
|    | 2.52 d (12.4) |  |
| 21 |  | na[c] |
| 22 | 4.42 dd (1.0, 8.9) | 82.30 |
| 23 | 3.70 m | 70.21 |
| 24 | 1.87 m | 32.54 |
|    | 2.26 td (2.8 13.0) |  |
| 25 | 5.11 ddd | 71.61 |
|    | (3.0, 4.3, 12.6) |  |
| 26 | 3.80 m | 67.87 |
| 27 | 1.08 d, 3H (6.7) | 18.00 |
| 28 | 0.88 s, 3H | 20.38 |
| 29 | 1.00 s, 3H | 16.42 |
| 30 | 5.75 bs | 113.80 |
| 31 |  | 167.45 |
| 32 | 1.04 s, 3H | 19.70 |
| 33 | 1.11 s, 3H | 23.23 |
| 34 | 5.82 bs | 114.16 |
| 35 |  | 169.48 |
| 36 | 3.65 s, 3H | 50.72 |
| 1' |  | 178.37 |

TABLE I-continued $^1$H and $^{13}$C NMR Data Obtained in CD$_3$CN for Bryostatin 20$^a$

| pos. | $^1$H δ (J in Hz) | $^{13}$C δ |
|---|---|---|
| 2' | | 38.74 |
| 3'–5' | 1.15 s, 9H | 26.28 |

$^a$ $^{13}$C Assignments made from HSQC and HMBC data.
$^b$Signal obscured.
$^c$Not assigned.

The composition, designated bryostatin 20 and illustrated in FIG. 6, may be presented for administration to humans and/or animals in unit dosage forms, alone or in combination with other compositions. It may be administered to humans and/or animals as a cancer fighting agent or for other purposes that are later discovered. Unite dosage forms such as tablets, capsules, pills, powders, granules, suppositories, solutions, suspensions, and the like may be used to administer the composition of the present invention to a human and/or animal. Unit dosages of the composition of the present invention may be produced from *Bugula neritina* species using current extraction methods or according to the methods and processes of the present invention.

Having thus described certain preferred embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method of collecting bryostatins, comprising:
   subjecting *Bugula neritina* larvae to a condition sufficient to cause an exudate comprising bryostatin; and
   collecting the *Bugula neritina* larvae exudate.

2. A method of collecting bryostatins, comprising:
   collecting larvae of *Bugula neritina*;
   stressing the larvae;
   collecting an exudate from the stressed larvae; and
   isolating bryostatins from the larvae exudate.

3. The method of claim 2, wherein collecting larvae of *Bugula neritina* comprises collecting living larvae of *Bugula neritina*.

4. The method of claim 2, wherein collecting larvae of *Bugula neritina* comprises collecting the larvae in an ocean environment.

5. The method of claim 2, wherein collecting larvae of *Bugula neritina* comprises collecting the larvae in a man-made aquacultural environment.

6. The method of claim 2, wherein collecting larvae of *Bugula neritina* comprises:
   transferring *Bugula neritina* from an ocean environment to a man-made aquacultural environment; and
   collecting larvae from the *Bugula neritina* in the man-made aquacultural environment.

7. The method of claim 2, wherein stressing the larvae comprises chemically stressing the larvae.

8. The method of claim 2, wherein stressing the larvae comprises chemically stressing the larvae with a salt solution selected from the group consisting of magnesium chloride solutions, potassium chloride solutions, and aqueous salt solutions.

9. The method of claim 2, wherein stressing the larvae comprises physically stressing the larvae.

10. The method of claim 2, wherein stressing the larvae comprises stressing the larvae to induce the exudation of bryostatins from the larvae.

11. A method of producing bryostatin, comprising:
    collecting larvae of *Bugula neritina*; and
    extracting bryostatin from said larvae.

12. The method of claim 11, wherein extracting bryostatin from said larvae comprises:
    collecting an exudate of the *Bugula neritina* larvae; and
    isolating bryostatins from the exudate.

13. The method of claim 12, further comprising, stressing the larvae of *Bugula neritina* to induce the larvae to exude bryostatins.

14. The method of claim 11, wherein extracting bryostatin from said larvae comprises:
    exposing said larvae to a solvent; and
    purifying said solvent to obtain bryostatin.

15. A method of harvesting bryostatin from the larvae of *Bugula neritina*, comprising:
    collecting exudate from the larvae of *Bugula neritina*; and
    isolating bryostatin from the exudate.

16. A purified compound of the formula:

17. A composition comprising a bryostatin compound of the formula:

obtained by a method comprising collecting exudate from the larvae of *Bugula neritina*.

* * * * *